(12) United States Patent
Aranyi et al.

(10) Patent No.: US 9,724,077 B2
(45) Date of Patent: Aug. 8, 2017

(54) APPARATUS FOR ENDOSCOPIC PROCEDURES

(71) Applicant: COVIDIEN LP, Mansfield, MA (US)

(72) Inventors: Ernest Aranyi, Easton, CT (US); Michael P. Whitman, New Hope, PA (US); Donald Malinouskas, Monroe, CT (US); David A. Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 267 days.

(21) Appl. No.: 14/157,939

(22) Filed: Jan. 17, 2014

(65) Prior Publication Data
US 2014/0135575 A1 May 15, 2014

Related U.S. Application Data

(63) Continuation of application No. 13/336,098, filed on Dec. 23, 2011, now Pat. No. 8,647,258, which is a
(Continued)

(51) Int. Cl.
*A61B 1/05* (2006.01)
*A61B 17/00* (2006.01)
(Continued)

(52) U.S. Cl.
CPC ........ *A61B 17/00234* (2013.01); *A61B 1/005* (2013.01); *A61B 1/00174* (2013.01);
(Continued)

(58) Field of Classification Search
CPC ....... A61B 1/042; A61B 1/05; A61B 1/00174; A61B 17/00234; A61B 90/361; A61B 1/005; A61B 1/0669; A61B 1/0676
See application file for complete search history.

(56) References Cited

U.S. PATENT DOCUMENTS 4,012,636 A * 3/1977 Engdahl ................ G01T 1/2978
250/363.02
6,211,904 B1 4/2001 Adair et al.
(Continued)

FOREIGN PATENT DOCUMENTS

EP 1759629 A1 3/2007
EP 1767139 A1 3/2007
(Continued)

OTHER PUBLICATIONS

Japanese Office Action dated Jun. 19, 2015 for Japanese Appln. No. JP 2014-132135.
(Continued)

*Primary Examiner* — John P Leubecker
*Assistant Examiner* — Rajaa El Alami

(57) ABSTRACT

The present disclosure provides for a surgical device. The surgical device includes a jaw assembly and a camera assembly coupled to the jaw assembly. The camera assembly includes a camera housing defining an interior space having at least one opening on a side thereof, first and second support arms pivotally coupled within the camera housing and deployable therefrom, and a camera body coupled to the first and second support arms and moveable between a first position, in which the camera body is positioned within the interior space of the camera housing, and a second position, in which the camera body extends from the at least one opening of the camera assembly.

19 Claims, 12 Drawing Sheets

Related U.S. Application Data continuation-in-part of application No. 12/352,397, filed on Jan. 12, 2009, now Pat. No. 8,771,169.

(60) Provisional application No. 61/020,298, filed on Jan. 10, 2008.

(51) Int. Cl.

| | | |
|---|---|---|
| *A61B 1/00* | (2006.01) | |
| *A61B 1/06* | (2006.01) | |
| *A61B 17/072* | (2006.01) | |
| *A61B 1/005* | (2006.01) | |
| *A61B 1/04* | (2006.01) | |
| *A61B 90/00* | (2016.01) | |
| *A61B 1/313* | (2006.01) | |
| *A61B 17/29* | (2006.01) | |
| *A61B 17/32* | (2006.01) | |
| *A61B 90/30* | (2016.01) | |

(52) U.S. Cl.
CPC ............... *A61B 1/042* (2013.01); *A61B 1/05* (2013.01); *A61B 1/0669* (2013.01); *A61B 1/0676* (2013.01); *A61B 17/07207* (2013.01); *A61B 90/361* (2016.02); *A61B 1/313* (2013.01); *A61B 90/30* (2016.02); *A61B 2017/0046* (2013.01); *A61B 2017/00398* (2013.01); *A61B 2017/00473* (2013.01); *A61B 2017/00482* (2013.01); *A61B 2017/00734* (2013.01); *A61B 2017/2905* (2013.01); *A61B 2017/2929* (2013.01); *A61B 2017/2943* (2013.01); *A61B 2017/320052* (2013.01)

(56) References Cited

U.S. PATENT DOCUMENTS

| | | | |
|---|---|---|---|
| 6,221,007 B1 | 4/2001 | Green | |
| 6,277,064 B1 | 8/2001 | Yoon | |
| 6,459,822 B1 | 10/2002 | Hathaway et al. | |
| 6,471,637 B1 | 10/2002 | Green et al. | |
| 6,648,816 B2 | 11/2003 | Irion et al. | |
| 6,793,652 B1 | 9/2004 | Whitman et al. | |
| 7,553,277 B2* | 6/2009 | Hoefig | A61B 1/00179 600/137 |
| 8,105,233 B2* | 1/2012 | Abou El Kheir | A61B 1/0008 348/47 |
| 8,647,258 B2 | 2/2014 | Aranyi et al. | |
| 9,125,552 B2* | 9/2015 | Dunki-Jacobs | A61B 1/00096 |
| 2003/0032863 A1 | 2/2003 | Kazakevich | |
| 2004/0094597 A1 | 5/2004 | Whitman et al. | |
| 2005/0021010 A1 | 1/2005 | Rothweiler et al. | |
| 2005/0234296 A1* | 10/2005 | Saadat | A61B 1/0008 600/129 |
| 2006/0020213 A1 | 1/2006 | Whitman et al. | |
| 2006/0184848 A1 | 8/2006 | Serizawa et al. | |
| 2007/0055103 A1 | 3/2007 | Hoefig et al. | |
| 2007/0073109 A1 | 3/2007 | Irion | |
| 2009/0054909 A1* | 2/2009 | Farritor | A61B 19/22 606/130 |
| 2009/0182193 A1 | 7/2009 | Whitman et al. | |
| 2009/0187072 A1* | 7/2009 | Manohara | A61B 1/00039 600/109 |
| 2009/0292164 A1 | 11/2009 | Yamatani | |
| 2009/0326322 A1 | 12/2009 | Diolaiti | |
| 2011/0121049 A1 | 5/2011 | Malinouskas et al. | |
| 2011/0230894 A1* | 9/2011 | Simaan | A61B 1/00183 606/130 |
| 2013/0282052 A1* | 10/2013 | Aranyi | A61B 17/07207 606/208 |

FOREIGN PATENT DOCUMENTS

| | | |
|---|---|---|
| EP | 2123225 A1 | 11/2009 |
| EP | 2324776 A2 | 5/2011 |
| JP | 2003500153 A | 1/2003 |
| JP | 2004537362 A | 12/2004 |
| JP | 2007-075604 A | 3/2007 |
| JP | 2009279411 A | 12/2009 |
| NO | 03013349 A2 | 2/2003 |
| WO | 0156460 A1 | 8/2001 |
| WO | 03063694 A1 | 8/2003 |
| WO | 2007016290 A2 | 2/2007 |
| WO | 2008033133 A2 | 3/2008 |
| WO | 2009039506 A1 | 3/2009 |
| WO | 2009089539 A1 | 7/2009 |
| WO | 2010042611 A1 | 4/2010 |

OTHER PUBLICATIONS

Canadian Office Action, dated Mar. 18, 2015 and Canadian Examination Search Report dated Mar. 10, 2015; corresponding to Canadian Patent Application No. 2,711,130; 8 total pages.
Canadian Office Action for Canadian Appln. No. CA 2,698,571 dated Oct. 16, 2015.
Canadian Office Action for CA 2,698,571 dated May 4, 2015.
European Search Report corresponding to European Application EP 11 00 1302.6; completed Apr. 27, 2011 and mailed May 4, 2011; 3 pages.
Extended European Search Report corresponding to EP 09701345.2, dated Nov. 20, 2012 (5 pp).
Extended European Search Report corresponding to EP 12 19 8737.4, completed Apr. 4, 2013 and mailed Apr. 12, 2013; (7 pp).
European Communication under Rule 71(3) EPC dated Mar. 24, 2015 for European Patent Appln. No. EP 10 010 188.0.
Japanese Office Action for JP 2014-132135 dated Dec. 4, 2015.
Australian Examination Report No. 1 corresponding to counterpart Int'l Appln. No. AU 2014204544, dated Feb. 19, 2016.
Australian Patent Examiner Report No. 1, dated Jun. 7, 2016, corresponding to Australian Application No. 2012258313; 5 pages.
Chinese Office Action (with English translation), corresponding to Chinese Application No. 201210567678.9, dated Nov. 30, 2015; 14 total pages.
Japanese Office Action (with English translation), dated Aug. 18, 2016, corresponding to Japanese Application No. 2012-279107; 10 total pages.
Australian Patent Examiner Report No. 2, dated Sep. 8, 2016, corresponding to Australian Application No. 2012258313; 3 pages.
Chinese Office Action (with English translation), dated Feb. 22, 2017, corresponding to Chinese Application No. 201210567678.9; 15 total pages.
Chinese Second Office Action (with English translation), corresponding to Chinese Application No. 201210567678.9, dated Aug. 1, 2016; 14 total pages.

* cited by examiner

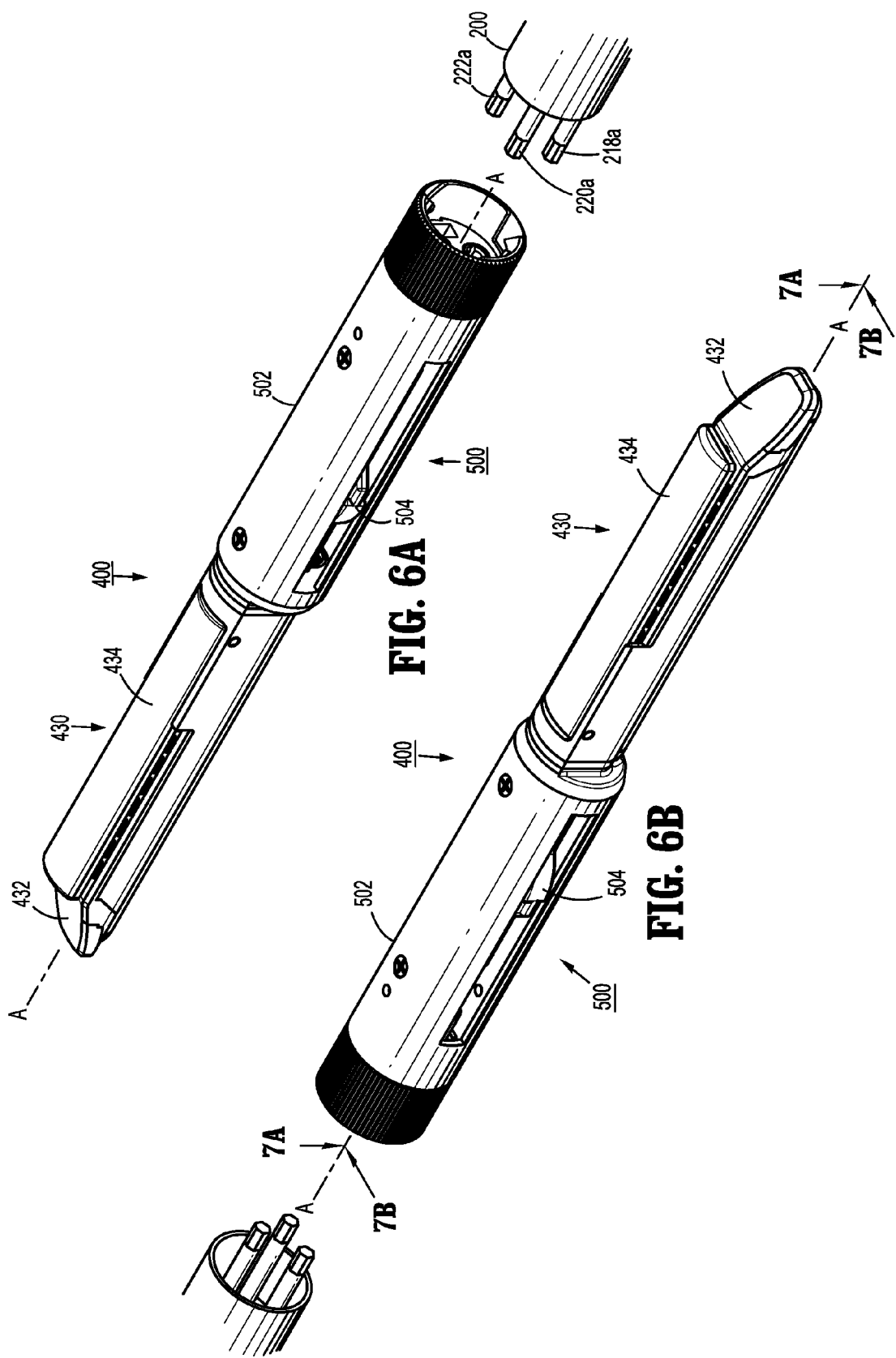

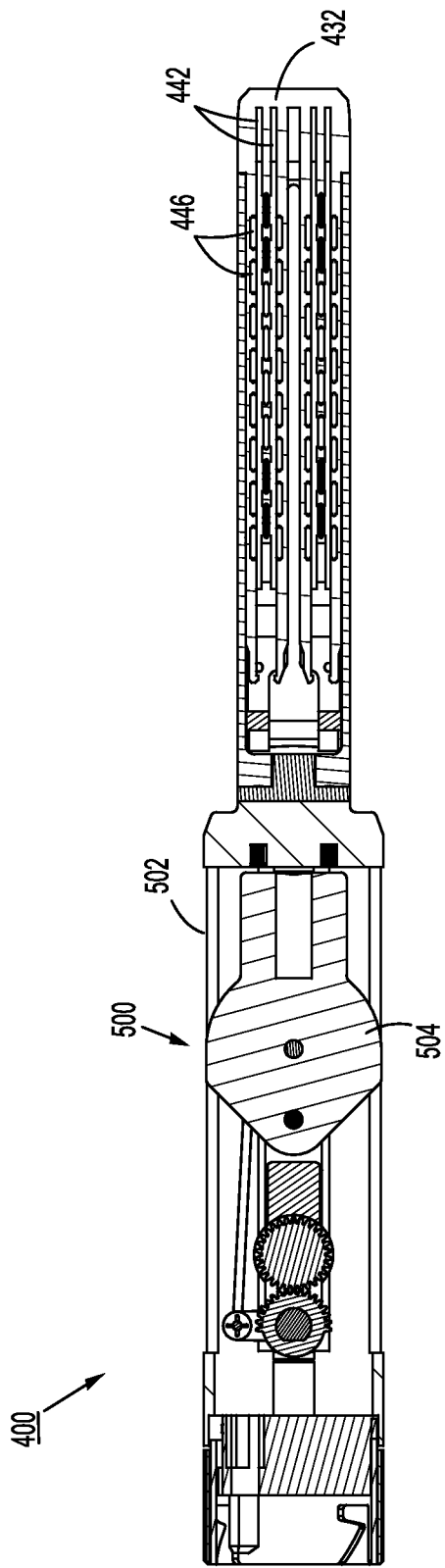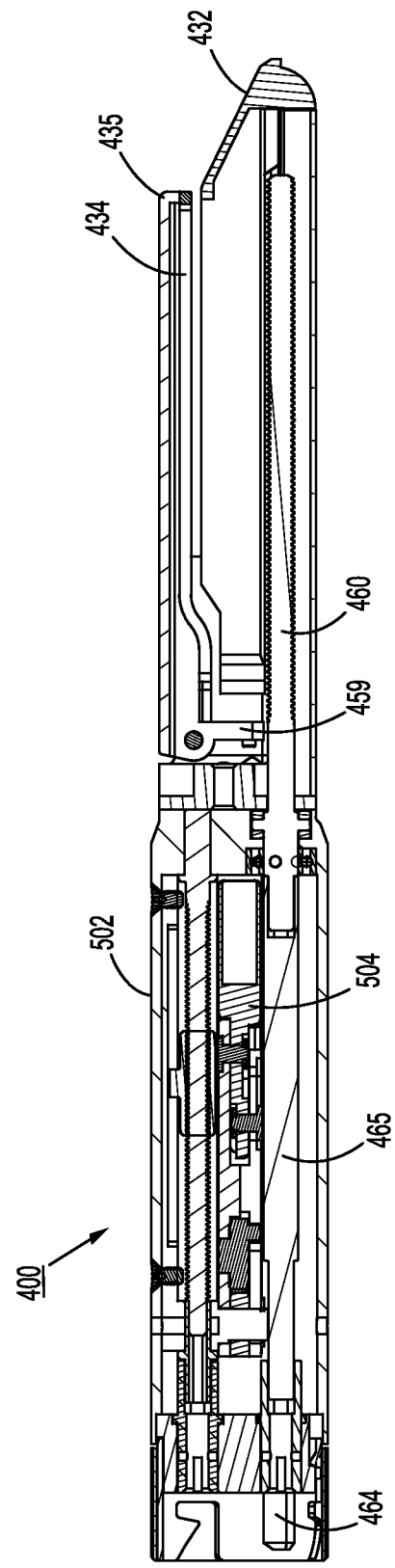
FIG. 7A
FIG. 7B

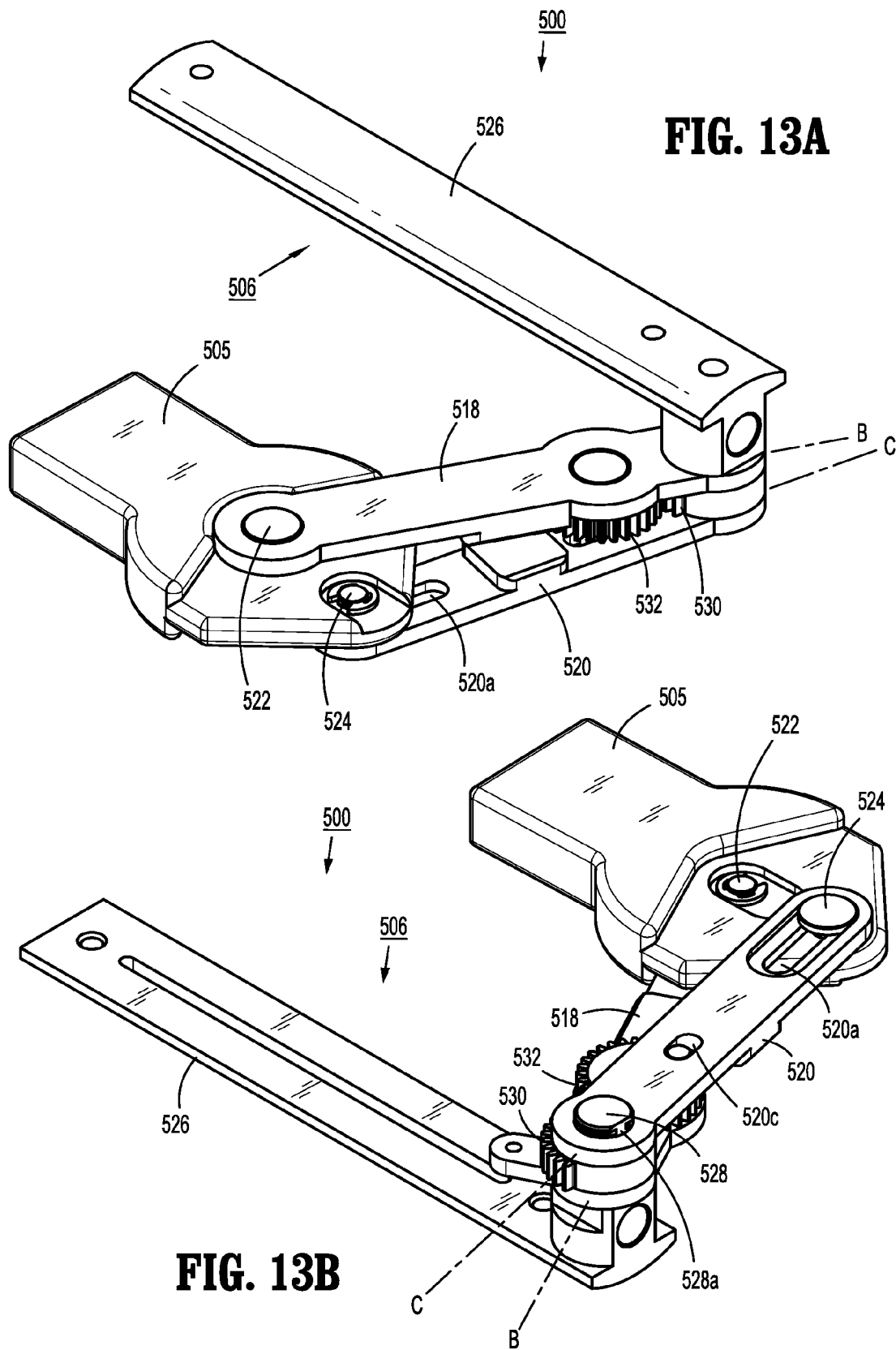

APPARATUS FOR ENDOSCOPIC PROCEDURES

CROSS-REFERENCE TO RELATED APPLICATIONS

The present application is a continuation of U.S. patent application Ser. No. 13/336,098, filed on Dec. 23, 2011, which is a continuation-in-part application and claims the benefit of and priority to U.S. patent application Ser. No. 12/352,397, filed on Jan. 12, 2009, which claims the benefit of and priority to U.S. Provisional Application No. 61/020, 298, filed on Jan. 10, 2008, the entire contents of all of which are incorporated by reference herein.

BACKGROUND

1. Technical Field

The present disclosure relates to surgical apparatuses, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating electromechanical surgical devices. In many instances the electromechanical surgical devices include a reusable handle assembly, and disposable or single use loading units. The loading units are selectively connected to the handle assembly prior to use and then disconnected from the handle assembly following use in order to be disposed of or in some instances sterilized for re-use.

Many of these electromechanical surgical devices are relatively expensive to manufacture, purchase and/or operate. There is a constant desire by manufactures and end users to develop electromechanical surgical devices that are relatively inexpensive to manufacture, purchase and/or operate.

In addition, the foregoing surgical devices do not include integrated imaging systems. As a result, a second device is used to provide images of the surgical site to the surgeon. The use of a second device may be more invasive and may require an operator to continually ensure that the surgical device and imaging device are coordinated, to provide adequate imaging.

Accordingly, a need exists for electromechanical surgical apparatus, devices and/or systems having improved imaging capabilities.

SUMMARY

Further details and aspects of exemplary embodiments of the present invention are described in more detail below with reference to the appended Figures.

According to one aspect of the present disclosure, a surgical device is disclosed. The surgical device includes a jaw assembly and a camera assembly coupled to the jaw assembly. The camera assembly includes a camera housing defining an interior space having at least one opening on a side thereof, first and second support arms pivotally coupled within the camera housing and deployable therefrom, and a camera body coupled to the first and second support arms and moveable between a first position, in which the camera body is positioned within the interior space of the camera housing, and a second position, in which the camera body extends from the at least one opening of the camera assembly.

According to another aspect of the present disclosure, a surgical instrument camera assembly is disclosed. The camera assembly includes a camera housing defining an interior space having at least one opening on a side thereof, first and second support arms pivotally coupled within the camera housing and deployable therefrom, and a camera body coupled to the first and second support arms and moveable between a first position, in which the camera body is positioned within the interior space of the camera housing, and a second position, in which the camera body extends from the at least one opening of the camera assembly.

According to a further aspect of the present disclosure. A surgical device is disclosed. The surgical device includes a jaw assembly and a camera assembly coupled to the jaw assembly. The camera assembly includes a camera housing defining an interior space having at least one opening on a side thereof; first and second support arms pivotally coupled within the camera housing and deployable therefrom; a first gear coupled to the camera housing; a second gear pivotally coupled to the first and second support arms; and a camera body coupled to the first and second support arms and moveable between a first position, in which the camera body is positioned within the interior space of the camera housing, and a second position, in which the camera body extends from the at least one opening of the camera assembly and is oriented toward the jaw assembly in response to pivoting of the first support arm.

Each of the above-described aspects may also include the following modifications. The camera body of the surgical device or the camera assembly may include at least one camera and at least one light source.

The camera housing of the camera assembly may include first and second openings on respective radially-opposed sides of the camera housing. The camera assembly of the surgical device or the camera assembly is moveable so as to extend from one of the first and second radially-opposed openings of the camera assembly.

The first and second support arms of the surgical device or the camera assembly are pivotally coupled at their proximal ends to the camera housing and at their distal ends to the camera body. In further embodiments, the surgical device or the camera assembly may also include a first gear coupled to the camera housing and a second gear mechanically engaged with the first gear and pivotally coupled to the first and second support arms. The first and second support arms are coupled to the camera body by first and second pins, respectively, and the second pin is disposed proximally of the first pin. The second support arm may also include a longitudinal slot and the second pin is configured to travel therethrough as the second support arm is pivoted.

The surgical device or the camera assembly may also include an actuation nut; a pivot arm having a proximal end pivotally coupled to the first support arm and a distal end pivotally coupled to the actuation nut; and a drive screw supported within the camera housing, wherein the actuation nut is threadably coupled to the drive screw such that rotation of the drive screw imparts longitudinal movement of the actuation nut thereby causing pivotal movement of the first support arm.

BRIEF DESCRIPTION OF THE DRAWINGS

Embodiments of the present disclosure are described herein with reference to the accompanying drawings, wherein:

FIG. 6A is a rear, perspective view of the end effector of FIG. 1, according to the present disclosure;

FIG. 6B is a front, perspective view of the end effector of FIG. 1, according to the present disclosure;

FIG. 7A is a top, longitudinal, cross-sectional view of the end effector of FIGS. 6A and 6B as taken through 7A-7A of FIG. 6A;

FIG. 7B is a side, longitudinal, cross-sectional view of the end effector of FIGS. 6A and 6B as taken through 7B-7B of FIG. 6A;

FIG. 13A is a perspective, top view of the camera assembly in a deployed configuration on the left side, according to the present disclosure; and FIG. 13B is a perspective, bottom view of the camera assembly in the deployed configuration on the right side, according to the present disclosure.

DETAILED DESCRIPTION OF EMBODIMENTS

Figure 1:
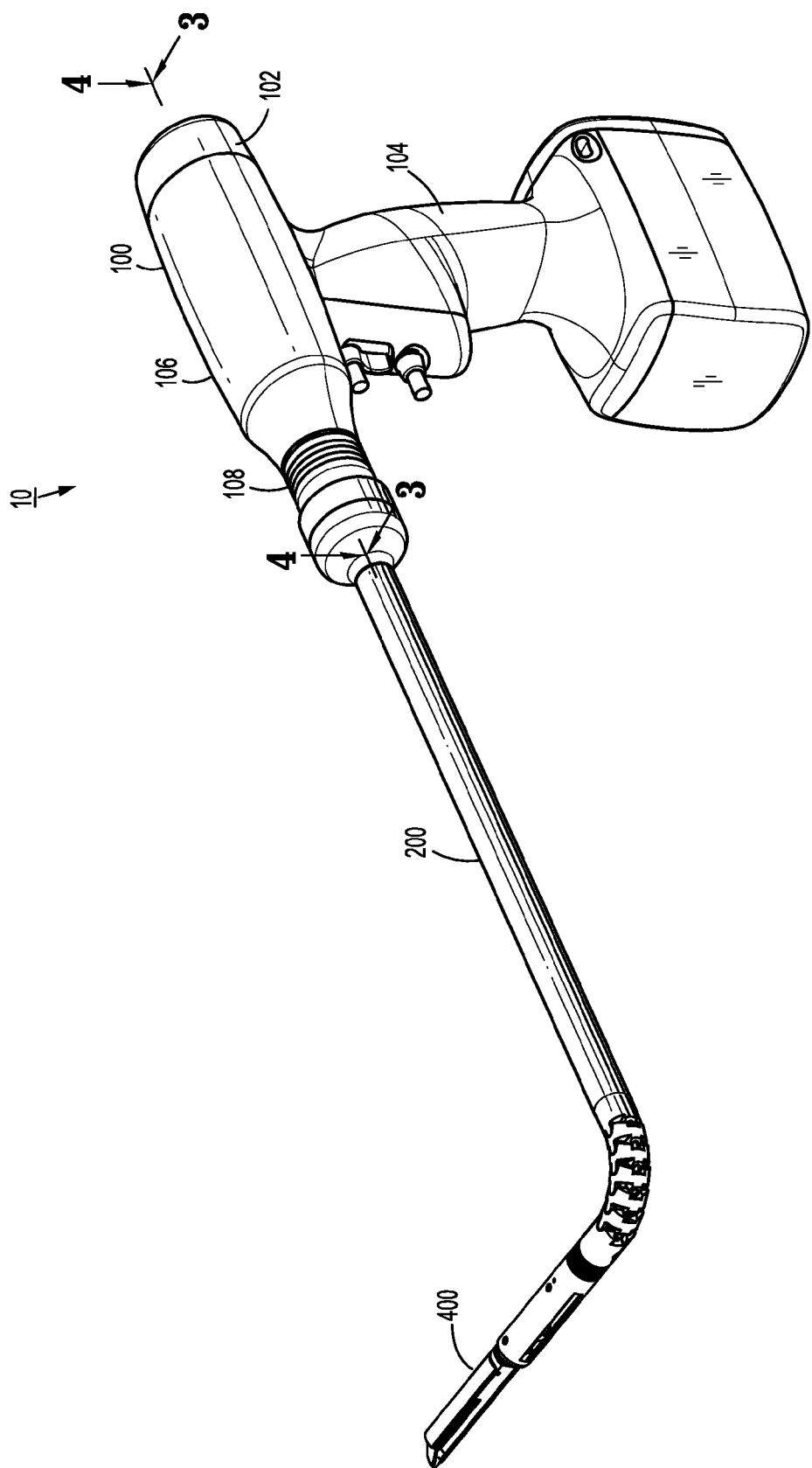
FIG. 1 is a perspective view of an electromechanical surgical system according to the present disclosure.
Figure 2:
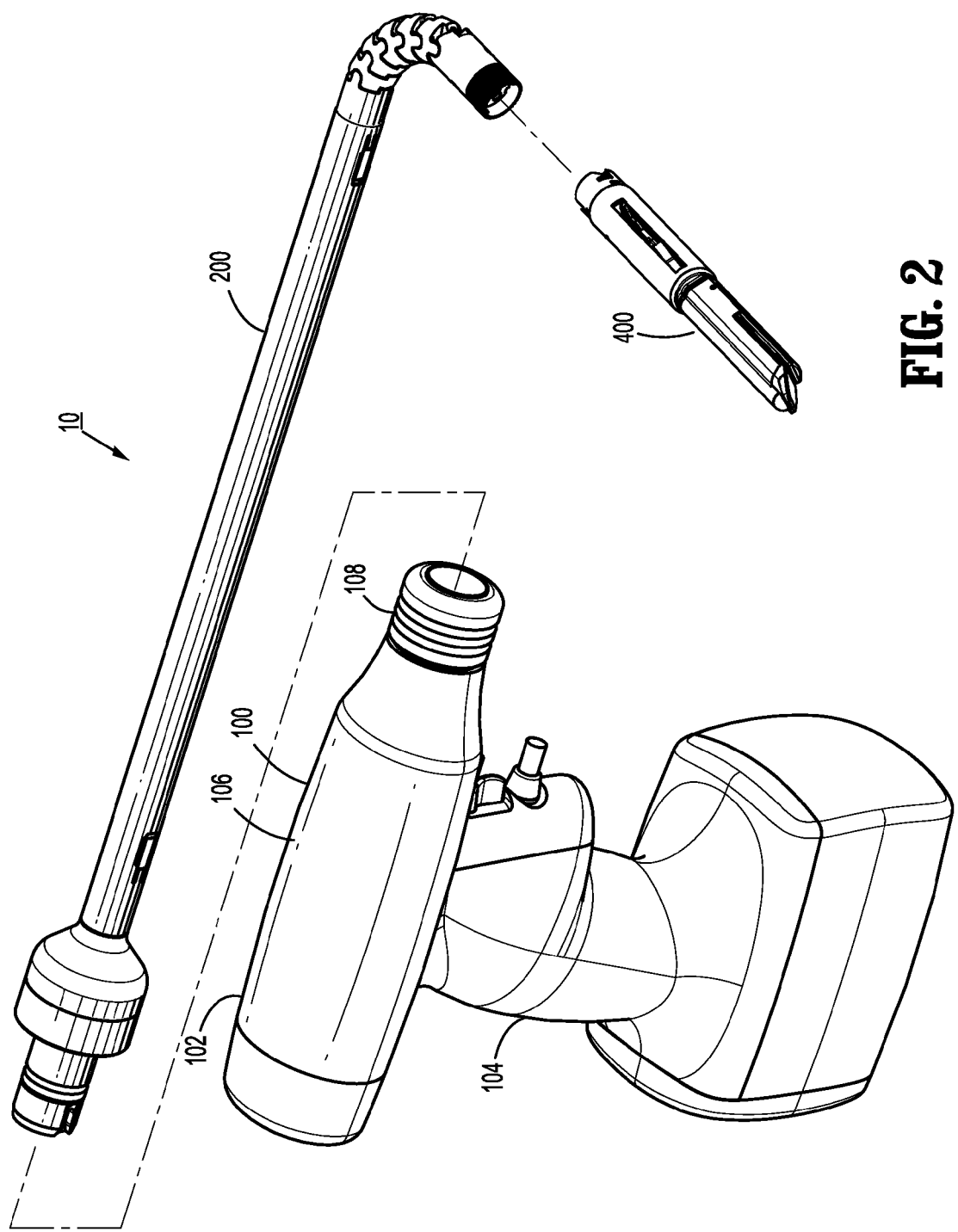
FIG. 2 is a disassembled, perspective view of a surgical instrument, an elongated member, and an end effector of the electrosurgical surgical system of FIG. 1, according to the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user. The terms "left" and "right" refer to that portion of the electromechanical surgical system, apparatus and/or device, or component thereof, that are on the left (e.g., port) and right (e.g., starboard) sides, respectively, from the perspective of the user facing the distal end of the electromechanical surgical system, apparatus and/or device from the proximal end while the surgical system, apparatus and/or device is oriented in non-rotational configuration.

Referring initially to FIGS. 1-5, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 400, via a shaft assembly 200. The end effector 400 and the shaft assembly 200 are configured for actuation and manipulation by the electromechanical, hand-held, powered surgical instrument 100. In particular, surgical instrument 100 is configured for selective connection with shaft assembly 200, and, in turn, shaft assembly 200 is configured for selective connection with any one of a plurality of different end effectors 400.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which is incorporated herein by reference, for a detailed description of the construction and operation of exemplary electromechanical, hand-held, powered surgical instrument 100.

Figure 3:
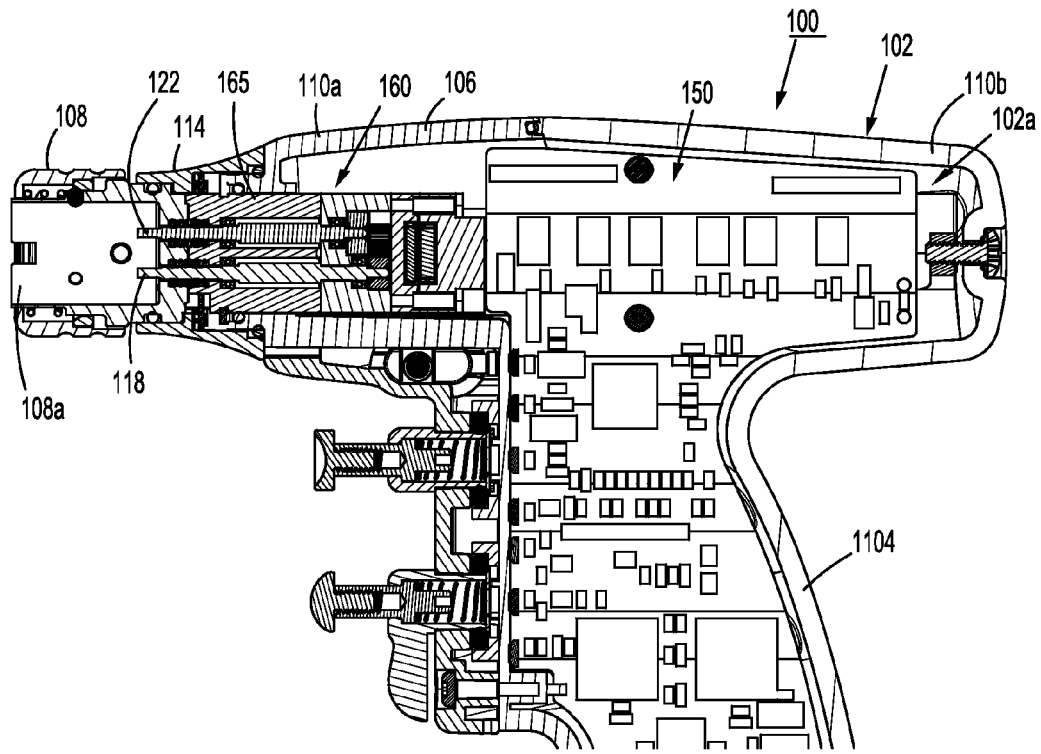
FIG. 3 is a side, cross-sectional view of a surgical instrument according to the present disclosure, as taken through 3-3 of FIG. 1, according to the present disclosure.
Figure 4:
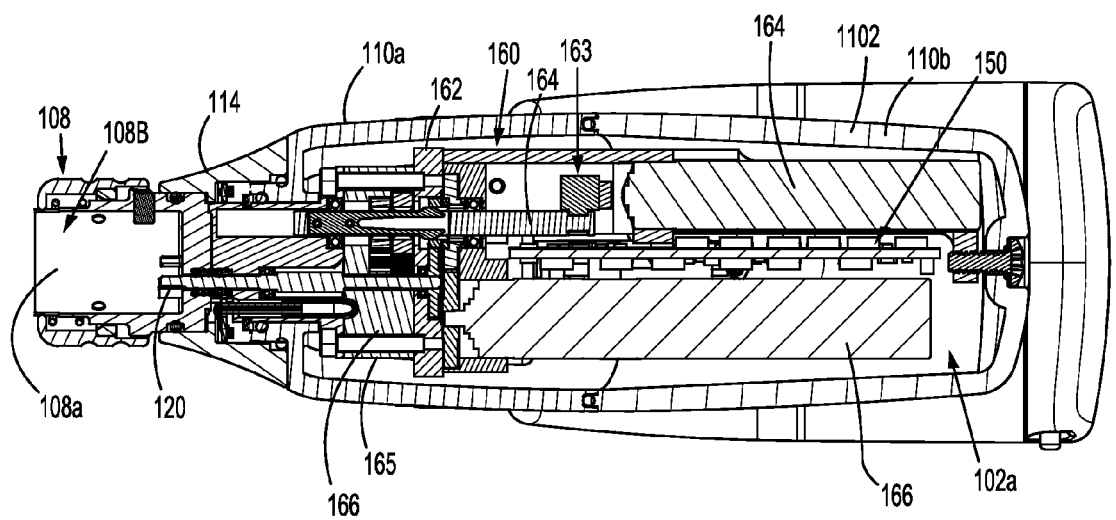
FIG. 4 is a top, cross-sectional view of the surgical instrument of FIG. 1, as taken through 4-4 of FIG. 1, according to the present disclosure.

Generally, as illustrated in FIGS. 1-4, surgical instrument 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners (FIGS. 3 and 4). When joined, distal and proximal half-sections 110a, 110b define the handle housing 102 having a cavity 102a therein in which a circuit board 150 and a drive mechanism 160 are disposed. The instrument 100 also includes a power source (not shown), which is coupled to the circuit board 150 and the drive mechanism 160. Circuit board 150 is configured to control the various operations of the instrument 100, in particular, the drive mechanism 160, as discussed in further detail below.

Lower housing portion 104 of the instrument 100 defines an aperture (not shown) formed in an upper surface thereof and which is located beneath or within intermediate housing portion 106. The aperture of lower housing portion 104 provides a passage through which wires and other various electrical leads interconnect electrical components (e.g., power source and any corresponding power control circuitry) situated in lower housing portion 104 with electrical components (e.g., circuit board 150, drive mechanism 160, etc.) situated in intermediate housing portion 106 and/or upper housing portion 108.

Figure 9A:
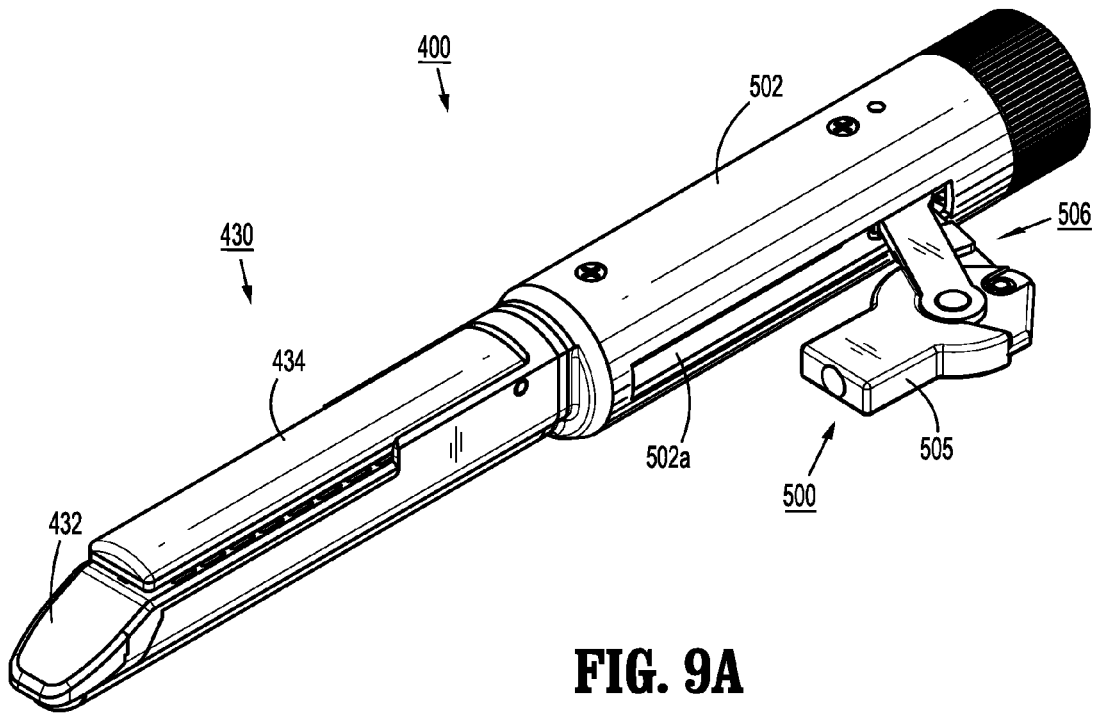
FIG. 9A is a front, perspective view of the end effector of FIG. 1, with a camera assembly deployed on a left side, according to the present disclosure.
Figure 9B:
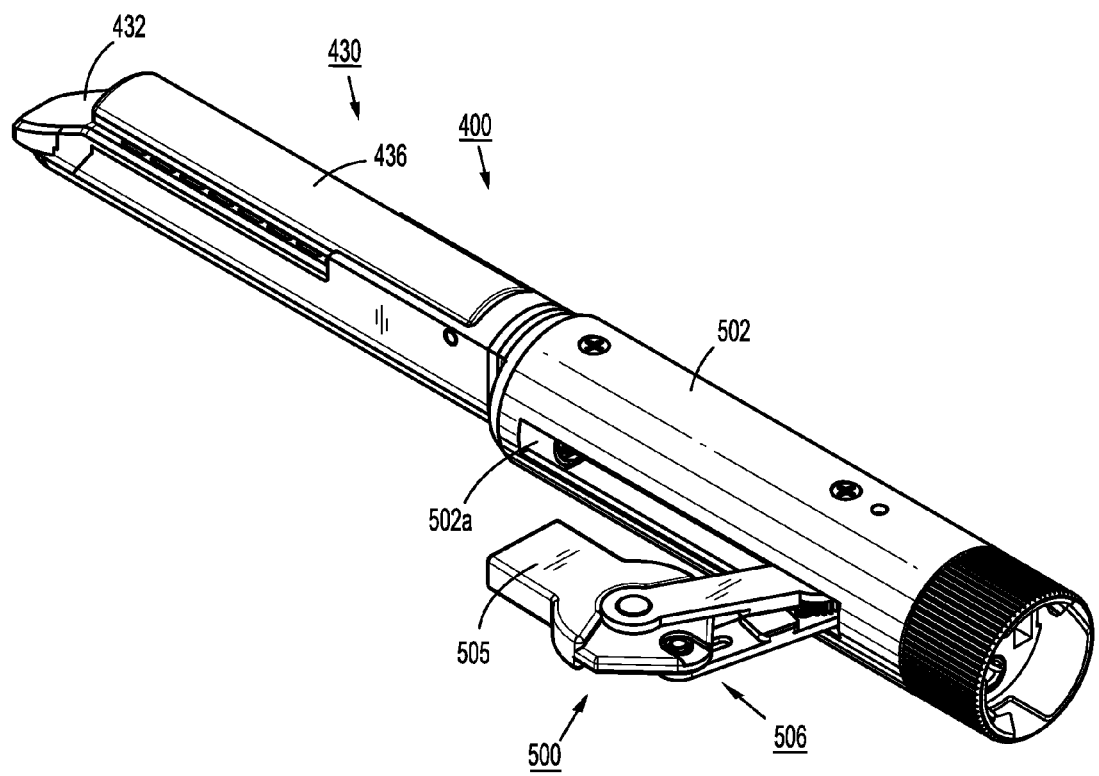
FIG. 9B is a rear, perspective view of the end effector of FIG. 1, with the camera assembly deployed on the left side, according to the present disclosure.
Figure 10A:
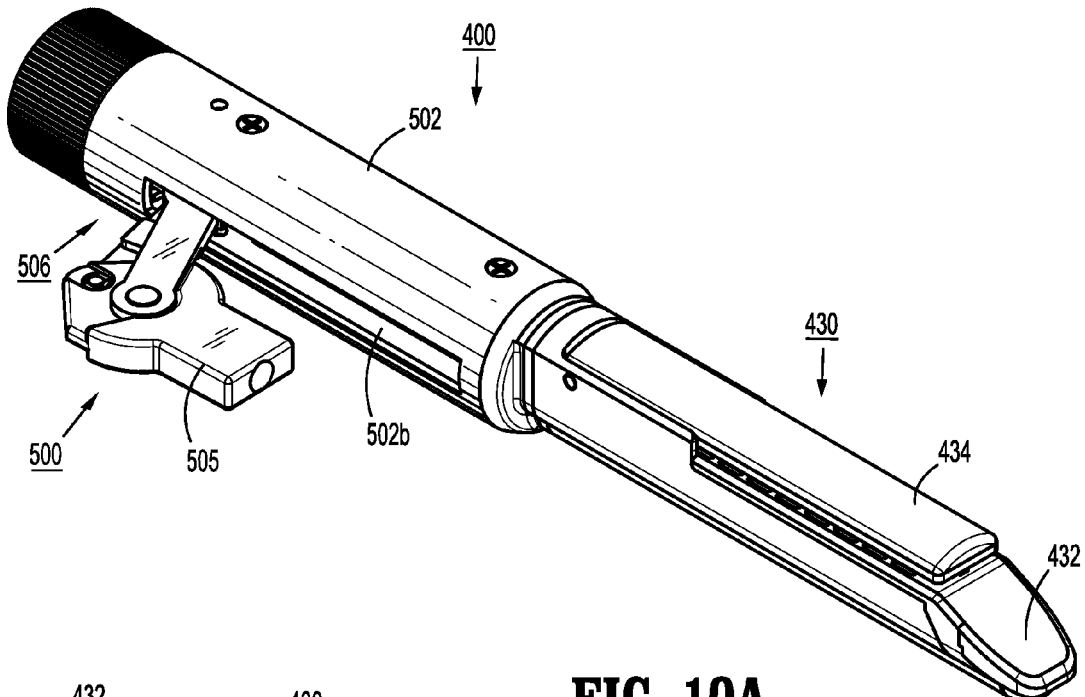
FIG. 10A is a front, perspective view of the end effector of FIG. 1, with the camera assembly deployed on a right side, according to the present disclosure.
Figure 10B:
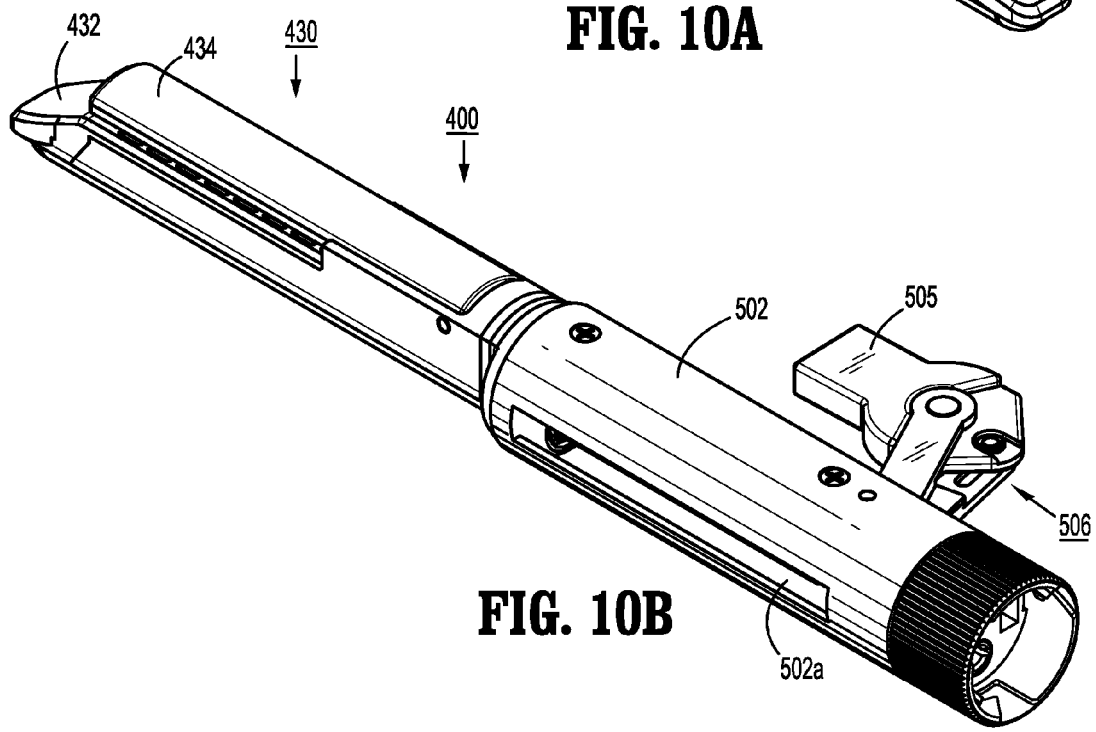
FIG. 10B is a rear, perspective view of the end effector of FIG. 1, with the camera assembly deployed on the right side, according to the present disclosure.
Figure 11A:
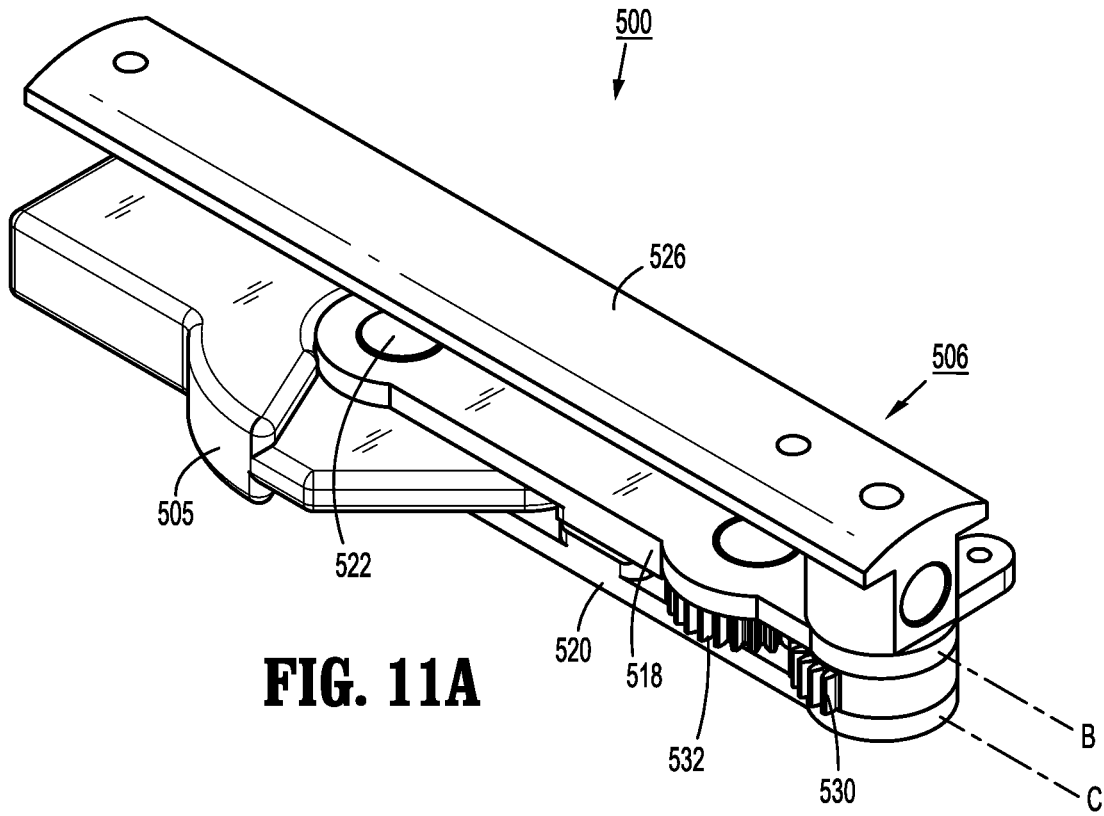
FIG. 11A is a perspective, top view of the camera assembly in a non-deployed configuration, according to the present disclosure.
Figure 11B:
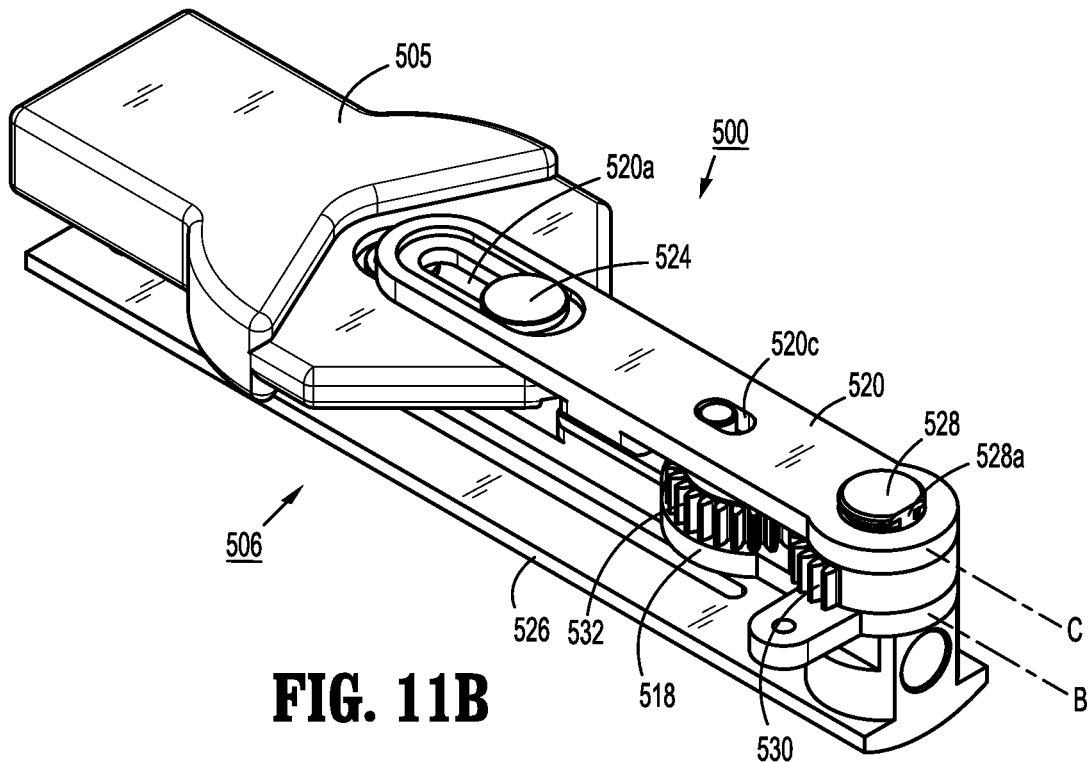
FIG. 11B is a perspective, bottom view of the camera assembly in the non-deployed configuration, according to the present disclosure.
Figure 12A:
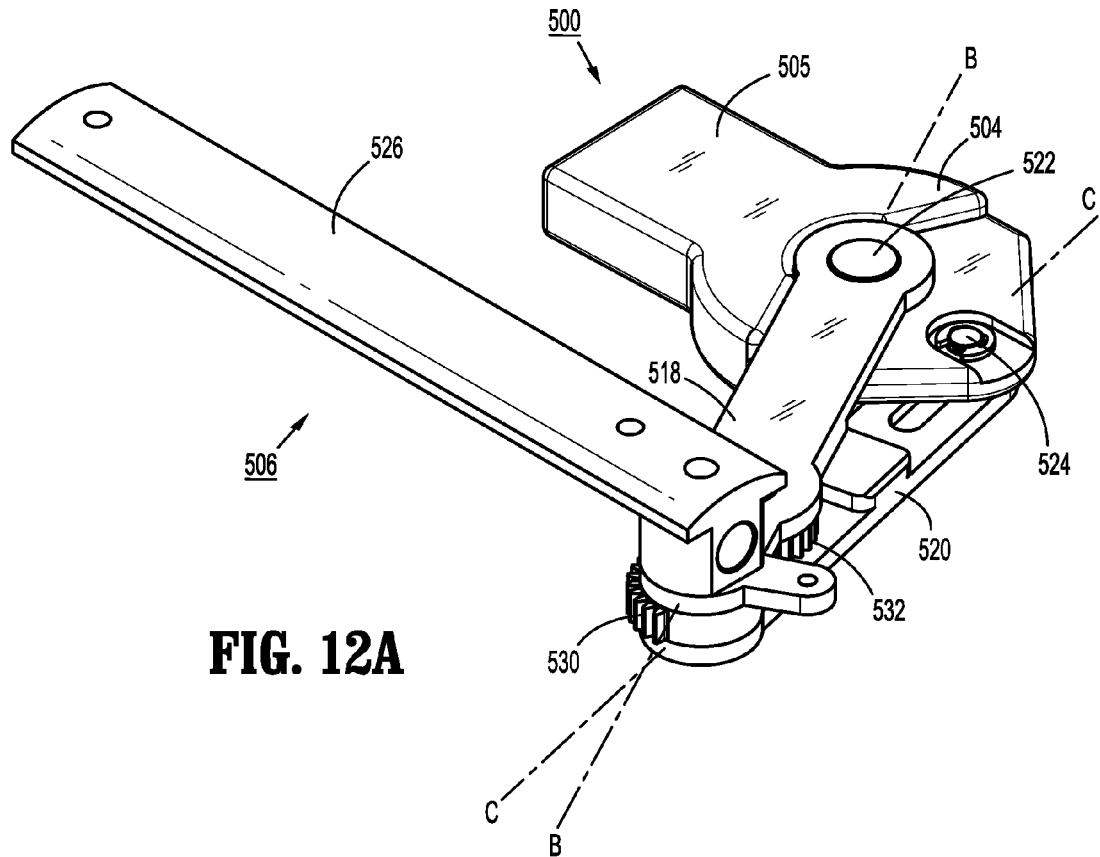
FIG. 12A is a perspective, top view of the camera assembly in a deployed configuration on the right side, according to the present disclosure.
Figure 12B:
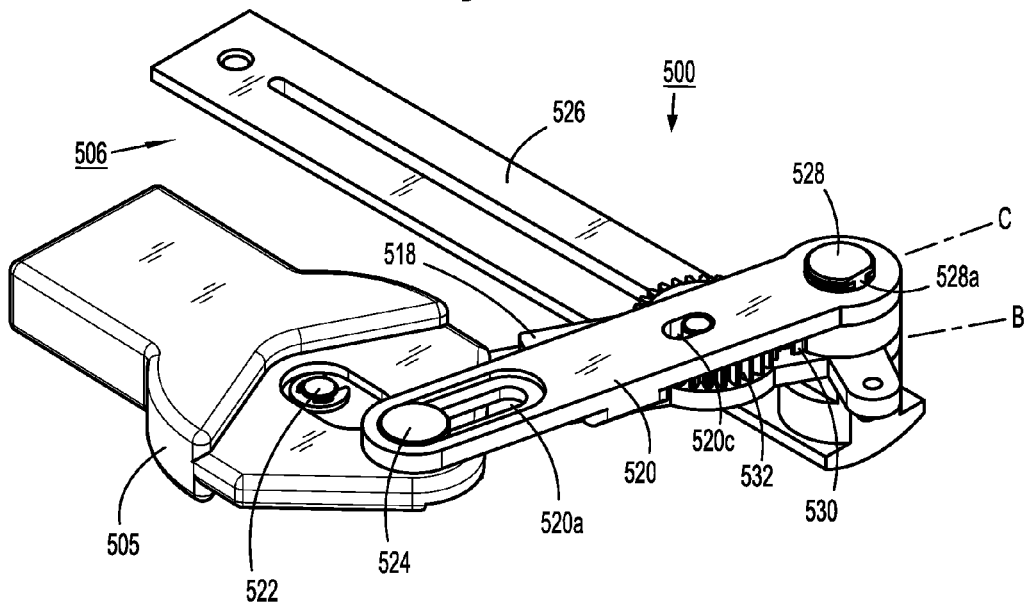
FIG. 12B is a perspective, bottom view of the camera assembly in the deployed configuration on the right side, according to the present disclosure.

With reference to FIGS. 3 and 4, distal half-section 110a of upper housing portion 108 defines a nose or connecting portion 108a. A nose cone 114 is supported on nose portion 108a of upper housing portion 108. Upper housing portion 108 of handle housing 102 provides a housing in which drive mechanism 160 is disposed. The drive mechanism 160 is configured to drive shafts and/or gear components in order to perform the various operations of instrument 100. In particular, drive mechanism 160 is configured to drive shafts and/or gear components in order to selectively rotate the end effector 400 about a longitudinal axis A-A (FIGS. 6A and 6B) relative to handle housing 102, to move jaw members of the end effector 400 relative to each other, and/or to fire the fasteners, to cut the tissue grasped within the end effector 400, and to pivot a camera assembly 500 (FIGS. 9A and 9B).

Figure 5:
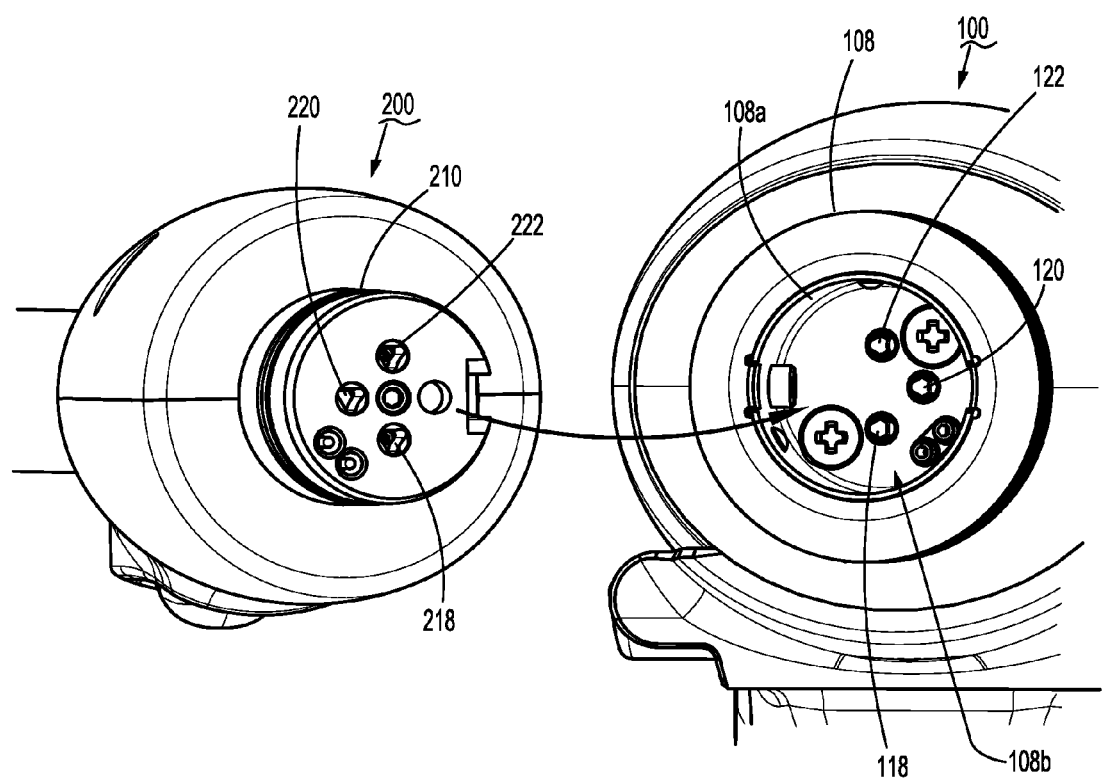
FIG. 5 is a front, perspective view of the surgical instrument of FIG. 1 with the elongated member of FIG. 2 separated therefrom, according to the present disclosure.

As seen in FIGS. 3 and 4, drive mechanism 160 includes a selector gearbox assembly 162 that is located immediately proximal relative to an elongated member 200. Proximal to the selector gearbox assembly 162 is a function selection module 163 having a first motor 164 that functions to selectively move gear elements within the selector gearbox assembly 162 into engagement with an input drive component 165 having a second motor 166. With particular reference to FIG. 5, the distal half-section 110a of upper housing portion 108 defines a connecting portion 108a configured to accept a corresponding drive coupling assembly 210 of the elongated member 200.

With continued reference to FIG. 5, the connecting portion 108a of instrument 100 includes a cylindrical recess 108b that receives a drive coupling assembly 210 of elongated member 200. Connecting portion 108a houses three rotatable drive connectors 118, 120, 122. When elongated member 200 is mated to instrument 100, each of rotatable drive connectors, namely, first drive connector 118, second drive connector 120, and third drive connector 122 of instrument 100, mechanically engage a corresponding rotatable connector sleeve, namely, first connector sleeve 218, second connector sleeve 220, and third connector sleeve 222 of elongated member 200.

The mating of drive connectors 118, 120, 222 of instrument 100 with connector sleeves 218, 220, 222 of elongated member 200 allows rotational forces to be independently transmitted via each of the three respective connector interfaces. The drive connectors 118, 120, 122 of instrument 100 are configured to be independently rotated by drive mechanism 160. In this regard, the function selection module 163 of drive mechanism 160 selects which drive connector or connectors 118, 120, 122 of instrument 100 is to be driven by the input drive component 165 of drive mechanism 160.

With continued reference to FIGS. 3 and 4, drive mechanism 160 includes a selector gearbox assembly 162 and a function selection module 163, located proximal to the selector gearbox assembly 162 that functions to selectively move gear elements within the selector gearbox assembly 162 into engagement with second motor 166. Thus, drive mechanism 160 selectively drives one or more of drive connectors 118, 120, 122 of instrument 100 at a given time.

Since each of drive connectors 118, 120, 122 of instrument 100 has a keyed and/or substantially non-rotatable interface with respective connector sleeves 218, 220, 222 of elongated member 200, when elongated member 200 is coupled to instrument 100, rotational force(s) are selectively transferred from drive mechanism 160 of instrument 100 to elongated member 200.

The selective rotation of drive connector(s) 118, 120 and/or 122 of instrument 100 allows instrument 100 to selectively actuate different functions of the end effector 400. In embodiments, any number of the drive connectors 118, 120, and/or 122 may be used to operate the end effector 400. As will be discussed in greater detail below, selective and independent rotation of first drive connector 118 of instrument 100 corresponds to the selective and independent opening and closing of the jaw members of the end effector 400, and driving of the actuation sled 440 (FIG. 8) of end effector 400. The selective and independent rotation of the third drive connectors 120, 122 of instrument 100 corresponds to the selective and independent pivoting of the camera assembly 500 rotation relative to the end effector 400. The drive connector 120 may be used to pivot and/or rotate the end effector 400 relative to the elongated member 200.

FIGS. 6A-8 illustrate components and operation of the end effector 400. The end effector 400 includes a jaw assembly 430 coupled at its proximal end to the camera assembly 500 having a camera housing 502. Jaw assembly 430 includes a pair of jaw members, which include a cartridge assembly 432 and an anvil 434. Cartridge assembly 432 houses one or more fasteners 433 (FIG. 8) that are disposed therewithin and is configured to deploy the fasteners 433. The anvil 434 is movably (e.g., pivotally) mounted to the end effector 400 and is movable between an open position, spaced apart from cartridge assembly 432, to a closed position wherein anvil 434 is in close cooperative alignment with cartridge assembly 432, to thereby clamp tissue.

Figure 8:
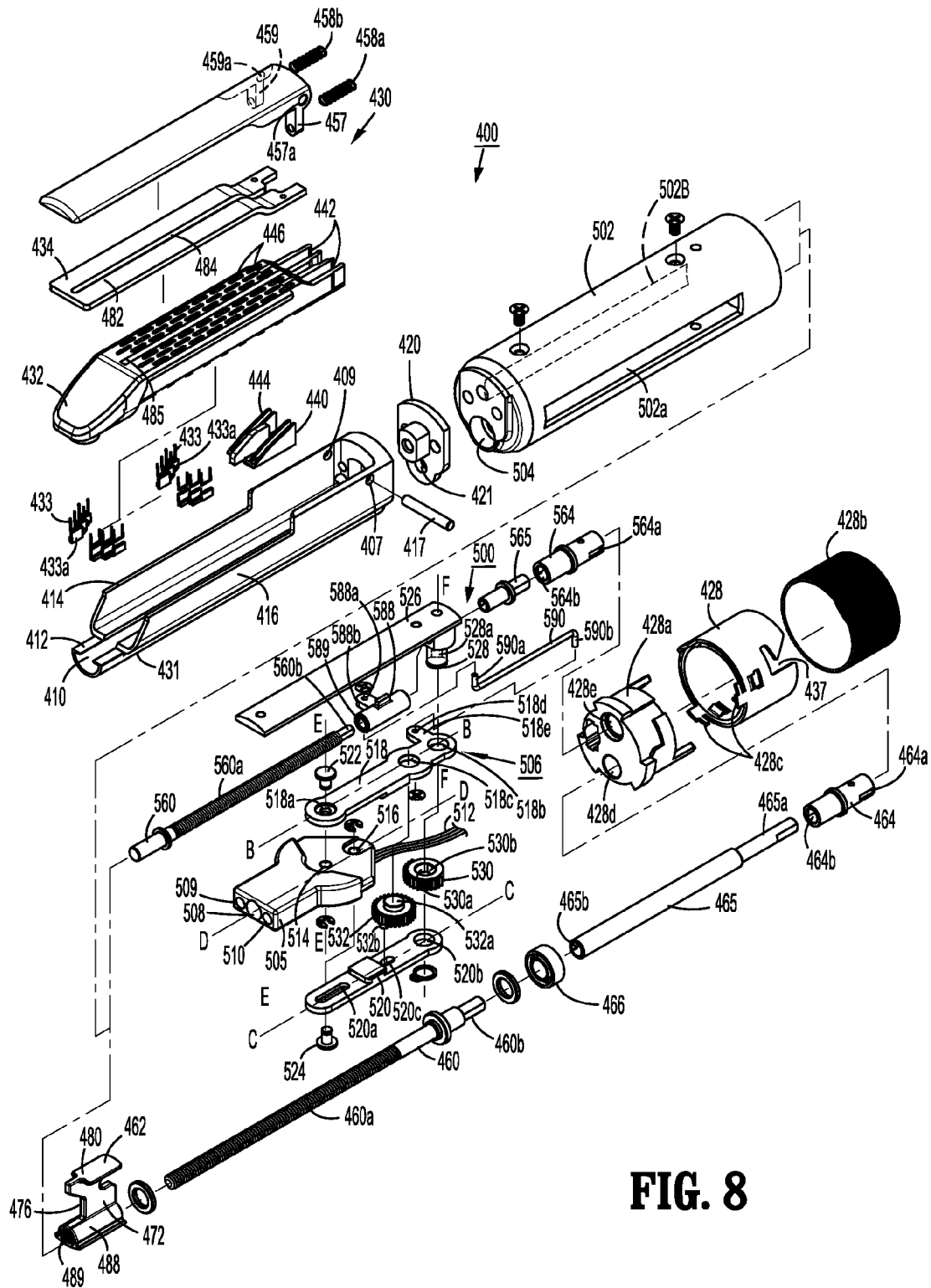
FIG. 8 is an exploded, perspective view of the end effector of FIG. 1, according to the present disclosure.

Referring to FIG. 8, an exploded view of the end effector 400 is shown. The jaw assembly 430 also includes a carrier 431 having an elongate channel 410 having a base 412 and two parallel upstanding walls 414 and 416 for supporting the cartridge assembly 432 and the anvil 434.

With continuing reference to FIG. 8, the distal portion of channel 410 supports cartridge assembly 432 which contains a plurality of surgical fasteners 433, which in embodiments may be of various sizes, e.g., about 30 mm in length and a plurality of corresponding ejectors or pushers 433a. Actuation sled 440 having upstanding cam wedges 444, exerts a fastener driving force on the pushers 433a, which, in turn, drive the fasteners 433 from cartridge assembly 432, as described in more detail below.

With reference to FIGS. 7A and 8, a plurality of spaced apart longitudinal slots 442 extend through cartridge assembly 432 to accommodate the upstanding cam wedges 444 of actuation sled 440. Slots 442 communicate with a plurality of transverse retention slots 446 within which the plurality of fasteners 433 and pushers 433a are respectively supported. During operation, as actuation sled 440 translates through cartridge assembly 432, the angled leading edges of cam wedges 444 sequentially contact pushers 433a, causing the pushers to translate vertically within slots 446, urging the fasteners 433 therefrom. The cartridge assembly 432 also includes a longitudinal slot 485 to allow for a knife blade to travel therethrough.

With reference to FIGS. 7B and 8, the jaw assembly 430 includes an anvil cover 435 disposed over the anvil 434. The anvil cover 435 protects tissue from being effected or acted upon by parts moving along the exterior of anvil 434. The anvil 434 along with the cover 435 is configured to remain in an open configuration until closed, as described in more detail below. The cover 435 also includes a pair of actuating shoulders 457 and 459 provided at a proximal end thereof.

The anvil 434 and the anvil cover 435 are pivotally coupled to the carrier 431. Each of the actuating shoulders 457 and 459 of the anvil cover 435 and the walls 414 and 416 of the carrier 431 also include openings 457a, 459a, 407, and 409, respectively. A pivot pin 417, or a pair of pins, passes through the openings 457a, 459a, 407, and 409. The carrier 431 is coupled to a mounting member 420, which is in turn coupled to the camera housing 502.

As shown in FIG. 8, biasing members 458*a* and 458*b*, which are shown as coil springs, are coupled to or otherwise secured within the mounting member 420. The biasing members 458*a* and 458*b* bear against internal bearing surfaces defined within mounting member 420 to bias anvil 434 into an open position, wherein the anvil 434 is spaced from cartridge assembly 432. In particular, as described above, the anvil 434 includes actuating shoulders 457 and 459 disposed at a proximal end thereof. Each of the actuating shoulders 457 and 459 abut the biasing members 458*a* and 458*b*, respectively, pushing the anvil 434 into the open position. As the anvil 434 is closed, the biasing members 458*a* and 458*b* are compressed against the mounting member 420.

With reference to FIGS. 6A-10B, the mounting member 420 is coupled to the distal end of the camera housing 502. Each of the mounting member 420 and the camera housing 502 include an opening 421 and 504, respectively, defined therethrough. The openings 421 and 504 are aligned with respect to each other when the mounting member 420 is coupled to the camera housing 502 (e.g., via bolts).

The end effector 400 also includes a coupling member 428 for coupling the end effector 400 to the elongated member 200. In particular, the coupling member 428 includes a mounting portion 428*a* and a ribbed sleeve 428*b*. The coupling member 428 is configured to be inserted over the mounting portion 428*a* and to secure the mounting portion 428*a* to the proximal end of the camera housing 502 via a plurality of bayonet connectors 428*c*. The ribbed sleeve 428*b* is inserted over the coupling member 428 and provides for a gripping surface during attachment and removal of the end effector 400 from the elongated member 200.

With continued reference to FIG. 8, the coupling member 428 includes one or more J-shaped slot 437 to align and couple the end effector 400 to the distal end of the elongated member 200. The slot 437 may define a conventional bayonet-type coupling which facilitates quick and easy engagement and removal of the end effector 400 from the elongated member 200. As shown in FIGS. 6A and 6B, the elongated member 200 includes three drive shafts 218*a*, 220*a*, 222*a*, which are coupled to or support respective ones of the connector sleeves 218, 220, 222 (FIG. 5). Once end effector 400 is connected to the elongated member 200, the first and third drive shafts 218*a* and 222*a* of elongated member 200 are engaged with the end effector 400 and provide for actuation of the end effector 400, as described in further detail below.

As seen in FIG. 8, end effector 400 further includes a first coupling 464 having a proximal opening 464*a* for mechanically engaging the first drive shaft 218*a* and a distal opening 464*b* for mechanically engaging a transmission link 465. The transmission link 465 includes a proximal male end 465*a* for engaging the distal opening 464*b* of the first coupling 464 and an opening 465*b* for mechanically engaging an axial drive screw 460.

Drive screw 460 is rotatably supported in carrier 431 and includes a threaded portion 460*a* and a proximal engagement portion 460*b*. Engagement portion 460*b* includes a multi-faceted or non-circular male connection (e.g., hexagonal) which is dimensioned and configured to engage the distal opening 465*b* of the transmission link 465. The drive screw 460 is disposed within the longitudinal slot the carrier 431, as shown in FIGS. 7B and 8. The drive screw 460 is rotatably secured at a distal end of the cartridge 432 and includes a bearing 466 frictionally fitted about the engagement portion 460*b*. This allows the drive screw 460 to be rotated relative to the carrier 431.

With continued reference to FIG. 8, a drive beam 462 is also disposed within the jaw assembly 430. The drive beam 462 includes a vertical support strut 472 and an abutment surface 476, including a knife for dissecting clamped tissue, which engages the actuation sled 440. The drive beam 462 also includes a cam member 480 disposed on top of the vertical support strut 472. Cam member 480 is dimensioned and configured to engage and translate with respect to an exterior camming surface 482 of the anvil 434 to progressively clamp the anvil against body tissue during firing.

A longitudinal slot 484 extends through the anvil 434 to accommodate the translation of the vertical strut 472. In embodiments, the anvil cover 435 may also include a corresponding longitudinal slot (not shown) formed on an underside thereof and is secured to an upper surface of anvil 434 to form a channel therebetween. This allows the cam member 480 to travel in between the cover 435 and anvil 434 during firing.

The drive beam 462 includes a travel nut 488 having a threaded bore 489 defined therethrough. The drive screw 460 is threadably coupled to the drive beam 462 through the bore 489, such that as the drive screw 460 is rotated, the drive beam 462 travels in a longitudinal direction along the axis A-A. As the drive screw 460 is rotated in a first direction (e.g., clockwise), the drive beam 462 travels in a distal direction closing the anvil 434 as the cam member 480 pushes down on the camming surface 482 thereof. The drive beam 462 also pushes the sled 440 in the distal direction, which then engages the pushers 433*a* via the cam wedges 444 to eject the fasteners 433*a*.

With reference to FIGS. 6A-13B, the camera assembly 500 is coupled to the jaw assembly 430 and is moveable between a first position, in which the camera assembly 500 is positioned within an interior space of the camera housing 502, and other positions, in which the camera assembly 500 extends at least partially through or from radially-opposed slots of the housing 502.

An example embodiment of the camera assembly 500 is shown in FIGS. 6A-13B. The camera assembly 500 is supported within the housing 502. The camera assembly 500 includes a camera body 505 and a deployment assembly 506 coupled thereto for deploying the camera body 505 from the housing 502. The camera body 505 is movable between a non-deployed position wherein the camera body 505 is disposed within the housing 500, as shown in FIGS. 6A and 6B, to at least one deployed position wherein the camera body 505 is at least partially exposed from the housing 500, as shown in FIGS. 9A-10B. The camera housing 500 includes two slots, a left slot 502*a* and a right slot 502*b*, defined on left and right radially-opposed sides thereof, respectively. In embodiments, the camera housing 502 may include a single slot. FIGS. 9A and 9B show the camera assembly 500 deployed from the left slot 502*a*, and FIGS. 10A and 10B show the camera assembly 500 deployed from the right slot 502*b*.

The camera body 505 defines a longitudinal axis D-D and includes a camera 508 and one or more light sources 509 and 510 configured to illuminate the area to be viewed by the camera 508. The camera 508 may be any suitable imaging apparatus configured for still or moving imaging including, but not limited to, digital devices, such as charge-coupled device (CCD) camera, a complementary metal-oxide-semiconductor (CMOS) sensor, an active-pixel sensor (APS), and analog devices, such as a vidicon tube. In embodiments, the camera 508 may also include any suitable lens or optical apparatus (e.g., optical fiber) for transmitting light to the above-described sensors.

The light sources 509, 510 may be LEDs, light bulbs, fiber optic elements and other devices capable of providing light generated remotely from the camera assembly 500. In embodiments, the camera body 505 may include two light sources 509, 510 located on either side of the camera 508.

The camera body 505 may also include one or more cables 512, here shown as a ribbon cable having multiple leads. The cable 512 may be connected, at one end, to the light sources 509, 510 and the camera 508, or may also be connected to other components of the camera assembly 500. A remote end of the cable 512 may be connected to a power source, a control device, a display, or any combination of those devices, or any other device.

With reference to FIGS. 8 and 11A-13B, the camera body 505 is pivotally coupled to first and second support arms 518 and 520 defining longitudinal axes B-B and C-C, respectively. The camera body 505 includes a first opening 514 and a second opening 516, the second opening 516 disposed proximally of the first opening 514. Each of the first and second support arms 518 and 520 also include distal openings 518a and 520a, respectively, disposed at their distal ends. The camera body 505 is coupled to the first support arm 518 via a first pin 522 passing through the first opening 514 and opening 518a defining a longitudinal axis E-E that is transverse to the axes A-A, B-B, C-C, and D-D. The camera body 505 is coupled to the second support arm 518 via a second pin 524 passing through the second opening 516 and opening 520a. The opening 520a has a substantially elongate or slot-like shape to allow for the pin 524 and the camera body 505 to travel in a longitudinal direction along the axis C-C.

The camera assembly 500 also includes a mounting bracket 526 disposed within the housing 502. The mounting bracket 526 is coupled to the housing 502 (e.g., via bolts) and includes a stem 528 defining a longitudinal axis F-F that is parallel to the axis E-E and transverse to the axes A-A, B-B, C-C, and D-D. Each of the first and second support arms 518 and 520 also include proximal openings 518b and 520b, respectively, disposed at their proximal ends. The first and second support arms 518 and 520 are pivotally coupled to the mounting bracket 526 about the stem 528 through the openings 518b and 520b.

The camera assembly 500 further includes a first or sun gear 530 having an opening 530a defined therein. The first gear 530 is disposed about or supported on stem 528. Each of the stem 528 and the opening 530a include one or more corresponding flat surfaces 528a and 530b, respectively. The flat surfaces 528a (FIGS. 11B, 12B, 13B) and 530a (FIG. 8) prevent rotational movement of the first gear 530 about the stem 528.

The first gear 530 is mechanically engaged with a second or planetary gear 532. Both of the gears 530 and 532 are disposed between the support arms 518 and 520. In particular, each of the first and second support arms 518 and 520 include openings 518c and 520c for rotatably coupling the second gear 532 therebetween. The second gear 532 includes a first stem 532a centrally disposed on a top surface thereof and a second stem 532b disposed off-center on a bottom surface thereof.

The first support arm 518 also includes an opening 518d disposed at the distal end thereof. In embodiments, the opening 518d of first support arm 518 may be disposed on an extension member 518e, which is offset in a lateral direction from the axis C-C to provide for better leverage.

With reference to FIG. 8, end effector 400 further includes a second coupling 564 having a proximal opening 564a for mechanically engaging another drive shaft (e.g., second or third drive shafts 220a, 222a) and a distal opening 564b for mechanically engaging a second axial drive screw 560. In embodiments, one or more additional couplings 565 may be included.

The drive screw 560 includes a threaded portion 560a and a proximal engagement portion 560b. Engagement portion 560b includes a multi-faceted or non-circular male connection (e.g., hexagonal) which is dimensioned and configured to engage the distal opening 564b of the second coupling 564 or the coupling 565. The drive screw 560 is disposed within the housing 502 and is rotatably secured at a distal end thereof, which allows the drive screw 560 to be rotated relative to the housing 502.

The deployment assembly 506 includes an actuation nut 588 having a threaded bore 589 defined therethrough. The drive screw 560 is threadably coupled to the actuation nut 588 through the bore 589, such that as the drive screw 560 is rotated, the actuation nut 588 travels in a longitudinal direction along the axis A-A.

A pivot arm 590 is pivotally coupled to both the actuation nut 588 and the first support arm 518. In particular, the pivot arm 590 includes a distal end 590a and a proximal end 590b. The distal end 590a of pivot arm 590 may have a substantially hook-like or L-shaped portion that is configured to pivotally couple to an opening 588a defined in an extension 588b of the actuation nut 588. The proximal end 590b of pivot arm 590 may also have a substantially similar shape as the distal end 590a and is configured to pivotally couple to the opening 518d of first support arm 518.

The pivotal configuration of the pivot arm 590 provides for pivoting of the first support arm 518, the second support arm 590, and the camera body 505. As the drive screw 560 is rotated in a first or clockwise direction, the actuation nut 588 travels in a distal direction. This results in the actuation nut 588 pulling the pivot arm 590 in the distal direction. Since the pivot arm 590 is coupled to the first support arm 518 at the opening 518d, which is disposed proximally of the opening 518c on the offset extension member 518e, pulling of the pivot arm 590 in the proximal direction results in pivoting of the first support arm 518 around the pivot stem 528 in a first or counterclockwise direction.

As the drive screw 560 is rotated in a second or counterclockwise direction, the actuation nut 588 travels in a proximal direction. This results in the actuation nut 588 pushing the pivot arm 590 in the proximal direction, which in turn pivots of the first support arm 518 around the pivot stem 528 in a second or clockwise direction.

Pivoting of the first support arm 518 provides for deployment of the camera body 505. As described above, the camera body 505 is pivotally coupled to the first support arm 518 via the pins 522, 524. Accordingly, as the support arm 518 is pivoted, the camera body 505 is deployed along therewith from the housing 502.

As the support arm 518 is pivoted about the stem 528, the second or planetary gear 532 rotates about the first or sun gear 530. Rotation of the planetary gear 532 is transferred to the second support arm 532, which results in pivoting thereof around the stem 528. In particular, the second stem 532b, which is disposed off-center on the bottom surface of the planetary gear 532 travels within the opening 520c. Rotational motion of the second stem 532b includes a radial (e.g., lateral) and an angular component, the angular component is transferred into longitudinal travel of the second stem 532b within the opening 520c, while the radial component is transferred into lateral movement of the second support arm 520, which pivots the arm 520 about the stem 528.

The gear ratio between the gears 530 and 532 allows the second support arm 520 to be rotated at a faster rate than the first support arm 518. As a result, the second support arm 520 has a wider range of travel (e.g., is disposed proximally of the first support arm 518). In particular, FIGS. 12A and 12B and FIGS. 13A and 13B show top and bottom views of the camera assembly 500 deployed on the right side and left side, respectively. In each deployed configuration (e.g., left or right) the second support arm 520 is pivoted beyond the first support arm 518. Consequently, the first and second support arms 518 and 520 are not in parallel (e.g., non-zero angle) alignment, namely, the longitudinal axis B-B is not in parallel alignment with the axis C-C. This pivoting relationship between the first and second support arm 518 and 520 allows for pivoting of the camera body 505 about the axis F-F, such that the longitudinal axis D-D is not in parallel alignment with either axis B-B or C-C, thus directing the camera body 505 toward the end effector 400.

The pivoting of the camera assembly 500 may be controlled manually by the operator or automatically. Manual operation of the camera assembly 500 may be accomplished by activating the drive shaft 222a by pressing a corresponding switch. During automatic operation, pivoting of the camera 500 may correspond to, e.g., be linked to, the articulation of the end effector 400 such that, when the end effector 400 is articulated, the camera assembly 504 is automatically moved in a corresponding manner that provides imaging of the end effector 400. This may be accomplished by linking the drive shafts 218a, 220a, 222a to operate concurrently. This ensures that the camera assembly 500 is continually oriented towards the end effector 400. At the same time, the rotation of the camera assembly 500 may be controlled by the operator in order to more finely control the area viewed.

It will be understood that various modifications may be made to the embodiments disclosed herein. For example, surgical instrument 100 need not apply staples but rather may apply two part fasteners as is known in the art. Further, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of preferred embodiments. Those skilled in the art will envision other modifications within the scope and spirit of the claims appended thereto.

What is claimed is:

1. A surgical device, comprising:
    an end effector including a distal end and a proximal end; and
    an imaging assembly coupled to the proximal end of the end effector, the imaging assembly including:
        a housing including at least one opening;
        a first support arm having a proximal end and a distal end;
        a second support arm having a proximal end and a distal end, the first and second support arms pivotally coupled at their proximal ends within the housing and pivotable about a pivot axis; and
        an imaging device coupled to distal ends of the first and second support arms and moveable between a first position, in which the imaging device is positioned within the housing, and a second position, in which the imaging device extends from the at least one opening of the housing and the end effector is within a field of view of the imaging device, wherein rotation of the first support arm in a first direction about the pivot axis and relative to the housing causes the second support arm to rotate about the pivot axis and relative to the first support arm in the first direction.

2. The surgical device according to claim 1, wherein the at least one opening includes first and second openings defined in respective radially-opposed sides of the housing.

3. The surgical device according to claim 2, wherein the imaging device is moveable so as to extend from one of the first and second openings of the imaging assembly.

4. The surgical device according to claim 1, wherein the first and second support arms are coupled to the imaging device by first and second pins, respectively, and wherein the second pin is disposed proximally of the first pin.

5. The surgical device according to claim 4, wherein the second support arm includes a longitudinal slot and the second pin is configured to travel through the longitudinal slot as the second support arm is pivoted.

6. The surgical device according to claim 1, further comprising a gear assembly coupled to the first and second support arms, the gear assembly is configured to provide for faster rotation of the second support arm relative to the first support arm about the pivot axis.

7. The surgical device according to claim 6, wherein the gear assembly includes a stationary gear coupled to the housing and a planetary gear mechanically engaged with the stationary gear and pivotally coupled to the first and second support arms.

8. The surgical device according to claim 1, the imaging assembly further including:
    a drive screw supported within the housing;
    an actuation nut threadably coupled to the drive screw; and
    a pivot arm having a proximal end pivotally coupled to the first support arm and a distal end pivotally coupled to the actuation nut, such that rotation of the drive screw imparts longitudinal movement of the actuation nut thereby causing actuation of the first support arm by the pivot arm.

9. The surgical instrument imaging assembly according to claim 1, wherein rotation of the second support arm relative to the first support arm in the first direction causes the imaging device to rotate relative to the first support arm and the second support arm in a second direction, opposite the first direction.

10. A surgical instrument imaging assembly, comprising:
    a housing defining at least one opening;
    a first support arm having a proximal end and a distal end;
    a second support arm having a proximal end and a distal end, the first and second support arms pivotally coupled at their proximal ends within the housing and pivotable about a pivot axis; and
    an imaging device coupled to distal ends of the first and second support arms and moveable between a first position, in which the imaging device is positioned within the housing, and a second position, in which the imaging device extends from the at least one opening of the housing and the end effector is within a field of view of the imaging device, wherein rotation of the second support arm relative to the first support arm in a first direction causes the imaging device to rotate relative to the first support arm and the second support arm in a second direction, opposite the first direction.

11. The surgical instrument imaging assembly according to claim 10, wherein the at least one opening includes first and second openings defined in respective sides of the housing.

12. The surgical instrument imaging assembly according to claim 10, wherein the first and second support arms are coupled to the imaging device by first and second pins, respectively, and the second support arm includes a longitudinal slot through which the second pin is configured to travel as the second support arm is pivoted, the second pin being disposed proximally of the first pin.

13. The surgical instrument imaging assembly according to claim 12, wherein the second support arm includes a longitudinal slot through which the second pin is configured to travel as the second support arm is pivoted and the second pin being disposed proximally of the first pin.

14. The surgical instrument imaging assembly according to claim 10, further comprising a gear assembly coupled to the first and second support arms, the gear assembly is configured to provide for faster rotation of the second support arm relative to the first support arm about the pivot axis.

15. The surgical instrument imaging assembly according to claim 14, wherein the gear assembly includes a stationary gear coupled to the housing and a planetary gear mechanically engaged with the stationary gear and pivotally coupled to the first and second support arms.

16. The surgical instrument imaging assembly according to claim 10, the imaging assembly further comprising:
 a drive screw supported within the housing;
 an actuation nut threadably coupled to the drive screw; and
 a pivot arm having a proximal end pivotally coupled to the first support arm and a distal end pivotally coupled to the actuation nut, such that rotation of the drive screw imparts longitudinal movement of the actuation nut thereby causing actuation of the first support arm by the pivot arm.

17. A surgical device, comprising:
 an end effector including a distal end and a proximal end; and
 an imaging assembly coupled to the proximal end of the end effector, the imaging assembly including:
  a housing including at least one opening;
  a first support arm having a proximal end and a distal end;
  a second support arm having a proximal end and a distal end, the first and second support arms pivotally coupled at their proximal ends within the housing and pivotable about a pivot axis;
  a gear assembly coupled to the first and second support arms, the gear assembly is configured to provide for faster rotation of the second support arm relative to the first support arm about the pivot axis; and
  an imaging device coupled to distal ends of the first and second support arms and moveable between a first position, in which the imaging device is positioned within the housing, and a second position, in which the imaging device extends from the at least one opening of the housing and the end effector is within a field of view of the imaging device, wherein rotation of the first support arm in a first direction about the pivot axis and relative to the housing causes the second support arm to rotate about the pivot axis and relative to the first support arm in the first direction.

18. The surgical instrument according to claim 17, wherein the gear assembly includes a stationary gear coupled to the housing and a planetary gear mechanically engaged with the stationary gear and pivotally coupled to the first and second support arms.

19. The surgical instrument according to claim 17, the imaging assembly further comprising:
 a drive screw supported within the housing;
 an actuation nut threadably coupled to the drive screw; and
 a pivot arm having a proximal end pivotally coupled to the first support arm and a distal end pivotally coupled to the actuation nut, such that rotation of the drive screw imparts longitudinal movement of the actuation nut thereby causing actuation of the first support arm by the pivot arm.

\* \* \* \* \*